United States Patent [19]

Granzer et al.

[11] Patent Number: 5,200,424

[45] Date of Patent: Apr. 6, 1993

[54] USE OF 10-MEMBERED RING LACTONES AS LIPID REGULATORS

[75] Inventors: Ernold Granzer, Kelkheim/Taunus; Peter Hammann, Babenhausen; Joachim Wink, Rödermark; Susanne Grabley, Königstein/Taunus, all of Fed. Rep. of Germany

[73] Assignee: Hoechst Aktiengesellschaft, Frankfurt am Main, Fed. Rep. of Germany

[21] Appl. No.: 749,869

[22] Filed: Aug. 26, 1991

[30] Foreign Application Priority Data

Aug. 28, 1990 [DE]  Fed. Rep. of Germany ....... 4027100

[51] Int. Cl.$^5$ ............................................ A61K 31/335
[52] U.S. Cl. ...................................... 514/450; 514/824
[58] Field of Search ............................. 514/450

[56] References Cited
PUBLICATIONS
CA113(1):4624f, Wink et al. (1989).

Primary Examiner—Frederick E. Waddell
Assistant Examiner—Kimberly R. Jordan
Attorney, Agent, or Firm—Curtis, Morris & Safford

[57] ABSTRACT

The compound of the formula

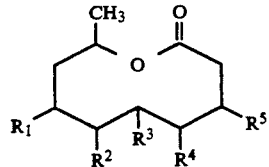

in which, independently of one another,
$R^1$ and $R^4$ are hydrogen or hydroxyl,
$R^2$ and $R^3$ are hydroxyl,
$R^5$ is hydrogen, hydroxyl or an oxo group, and
$R^2$ and $R^3$, and $R^3$ and $R^4$, can each together form a double bond, has hypolipemic properties and is used for the preparation of a pharmaceutical for lowering serum cholesterol.

3 Claims, No Drawings

USE OF 10-MEMBERED RING LACTONES AS LIPID REGULATORS

DESCRIPTION

Elevated serum cholesterol concentrations alone, or with simultaneously elevated serum triglycerides, represent a risk factor for arteriosclerosis which may be manifested in particular in the form of coronary sclerosis, of myocardial infarct, peripheral vascular occlusions, but also in the form of apoplexy in the region of the brain. On the other hand, it is known from many studies that a normalization or lowering of the elevated serum cholesterol levels may decisively reduce this risk. This can be effected to a limited extent by dietetic measures and to a greater extent by drug therapy. It is likewise possible to induce regression of arteriosclerotic vascular changes which are already present, as long as they have not yet entered an irreparable stage (direct calcification) by greatly diminishing a very much elevated serum total cholesterol.

In the Western world, where dietetic faults have persisted for decades, deaths in the population are attributable indirectly or directly to arteriosclerosis in almost 50% of cases or more. It is therefore extremely desirable to develop highly effective medicaments for reducing serum cholesterol, which are at the same time well tolerated. Available for this in the past have been medicaments of the type of the fibrates, of nicotinic acid, of non-absorbable bile acid sequestrants, probucol and, especially in recent years, of competitive HMG-CoA reductase inhibitors, for example of the type of lovastatin (Endo, A. J., J. Med. Chem. 28, 401 (1985)).

It has now been found, surprisingly, that 10-membered ring lactones can reduce the serum cholesterol level.

Thus the invention relates to the use of the compound of the formula I

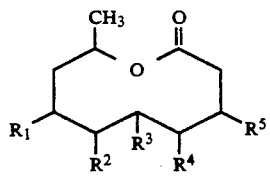

in which, independently of one another, $R^1$ and $R^4$ are hydrogen or hydroxyl, $R^2$ and $R^3$ are hydroxyl, $R^5$ is hydrogen, hydroxyl or an oxo group, and $R^2$ and $R^3$, and $R^3$ and $R^4$, can each together form a double bond, for the preparation of a pharmaceutical for lowering serum cholesterol.

The invention is described in detail hereinafter, especially in its preferred embodiments. The invention is furthermore defined by the contents of the claims.

EP 333,024 describes the obtaining of the compound of the formula I. Penicillium strains, preferably DSM 4209 and 4210, synthesize this compound in conventional fermentation solutions. They can be isolated by extraction of mycelium and culture broth with organic solvents and subsequent purification by chromatography.

The compound of the formula I has hypolipemic properties. The atherogenic lipoproteins VLDL and LDL in the serum are greatly reduced by the compound, while the effect on vasoprotective HDL is only weak. The vasoprotective index HDL-chlolesterol: LDL-cholesterol is greatly increased in this way.

The hypolipemic effect of the compound of the formula I was established in the following investigation:

Male rats with an initial weight above 180 g received the test product of the formula I in polyethylene glycol 400 by gavage once a day (in the morning) (0.5 ml/100 g of body weight); the relevant control group received only the same amount of solvent. The last (7th) administration took place 24 hours before blood sampling and sacrifice. There was free access to feed and water during the test. Feed was withdrawn 24 hours before the retroorbital blood sampling, which took place under light ether anesthesia before and after the treatment period (that is to say on the 1st and 8th day). Serum glutamic-oxalate transaminase (SGOT), serum glutamic-pyruvic transaminase (SGPT), alkaline phosphatase (aP), bilirubin and creatinine were determined in the serum of each individual animal. The total glycerol was measured from the pooled serum of all animals in a group as measure of the triglycerides (Eggstein, M. Kreutz, F. H.: Klin. Wschr. 44, 262 and 267 (1966); Wahlefeld, A. W., in: H. O. Bergmeier: Methoden der enzymatischen Analyse (Methods of enzymatic analysis), 2nd Edition, Volume II, Verlag Chemie 1974, Page 1878). Immediately after the blood sampling the animals were sacrificed by distortion of the spinal column. The livers were removed, and the relative liver weight was determined. In addition, the body weight gain and the feed consumption were investigated. The statistical analysis was carried out by Student's t test.

To analyze the serum lipoproteins, after the treatment period the serum of all rats in a group was pooled. The serum lipoproteins were separated using a preparative ultracentrifuge (Kontron TGA, Beckmann 50.4 Ti rotor).

The flotation of the serum lipoproteins (Koga, S., Horwith, D. L., and Scanu, A. M.: Journal of Lipid Research 10, 577 (1969), Havel, R. J., Eder, H. A., and Bragdon, H. H.: J. Clin. Invest. 34, 1345 (1955)) was carried out at the following densities:

| | | | |
|---|---|---|---|
| 1. | VLDL | density | <1.006 |
| 2. | LDL | density | 1.006 to 1.04 |
| 3. | HDL | density | 1.04 to 1.21 |

Assay kits from Boehringer/Mannheim were used for enzymatic determination of cholesterol by the CHOD-PAP high performance method (Siedel, J. Schlumberger, H., Klose, S., Ziegenhorn, J., and Wahlefeld, A. W.: J. Clin. Chem. Clin. Biochem. 19, 838 (1981)) and of the triglycerides by fully enzymatic determination (Eggstein, M. Kreutz, F. H.: Klin. Wschr. 44, 262 and 267 (1966); Wahlefeld, A. W., in: H. O. Bergmeier: Methoden der enzymatischen Analyse (Methods of enzymatic analysis), 2nd Edition, Volume II, Verlag Chemie 1974, Page 1878) in the separate lipoprotein fractions; protein was determined by the method of Lowry et. al. (Lowry, O. H., Roseborough, N. J., Farr, A. L., J. Biol. Chem. 193, 265 (1951)).

The results for the preferred compound of the formula I in which $R^1$, $R^4$ and $R^5$ are hydroxyl, and $R^2$ and $R^3$ together form a double bond, are listed in Tables 1 to 3 in the examples.

The compound of the formula I can be used for the prophylaxis and treatment of diseases based on an elevated cholesterol level, especially coronary heart diseases, arteriosclerosis and similar diseases. The invention also relates to pharmaceutical compositions of the compound of the formula I.

In the preparation of pharmaceuticals it is possible to use, besides the active substance, also pharmaceutically acceptable additives such as diluents and/or excipient materials. By this are meant physiologically acceptable substances which convert the active substance, after mixing therewith, into a form suitable for administration.

Examples of suitable solid or liquid pharmaceutical presentations are tablets, coated tablets, powders, capsules, suppositories, syrups, emulsions, suspensions, drops or injectable solutions, and products with protracted release of active substance. Examples of frequently used excipients or diluents which may be mentioned are various sugars or types of starch, cellulose derivatives, magnesium carbonate, gelatin, animal and vegetable oils, polyethylene glycols, water or other suitable solvents, and water-containing buffers which can be made isotonic by addition of glucose or salts.

It is additionally possible to use, where appropriate, surface-active agents, colorings and flavorings, stabilizers and preservatives as further additives in the pharmaceutical compositions according to the invention. It is also possible to use pharmacologically acceptable polymeric carriers such as, for example, polyphenylpyrrolidones, or other pharmaceutically acceptable additives such as, for example, cyclodextrin or polysaccharides. The compounds can, in particular, also be combined with additives which bind bile acid, especially nontoxic, basic anion exchanges which are not absorbable in the gastrointestinal tract.

The products can be administered orally, rectally or parenterally. It is possible and preferable for the products to be prepared in dosage units; in particular, tablets, capsules, suppositories represent examples of suitable dosage units. Each dosage unit, especially for oral administration, can contain up to 1,000 mg, but preferably 10 to 100 mg, of the active component. However, it is also possible to use dosage units above or below this, which should, where appropriate, be divided or multiplied before administration.

It is possible, where appropriate, for the dosage units for oral administration to be microencapsulated in order that release is delayed or extended over a longer period, such as, for example, by coating or embedding the active substance in particle form in suitable polymers, waxes or the like.

Parenteral administration can take place using liquid dosage forms such as sterile solutions and suspensions which are intended for intramuscular or subcutaneous injection. Dosage forms of this type are prepared by dissolving or suspending an appropriate amount of active substance in a suitable physiologically acceptable diluent such as, for example, an aqueous or oily medium and sterilizing the solution or suspension, where appropriate also using suitable stabilizers, emulsifiers and/or preservatives and/or antioxidants.

The oral administration form is preferred, especially from the viewpoint of a long duration of therapy, and represents a considerable facilitation in the prevention and therapy of the diseases mentioned above.

The pharmaceutical products are prepared by generally customary processes. The dosage regimen may depend on the type, age, weight, sex and medical condition of the patient or person at risk.

The invention is illustrated further hereinafter by means of examples.

EXAMPLES

TABLE 1

Rat, male, strain: HOE WISKf (SPF 71), lipoprotein fractionation by ultracentrifugation.

| Compound | Dose mg/kg/day | % Change compared with control | | | | | | Cholesterol | |
|---|---|---|---|---|---|---|---|---|---|
| | | Total cholesterol | | | Protein | | Triglycerides | HDL | Based on |
| | | VLDL | LDL | HDL | VLDL | LDL | VLDL | LDL | control |
| Formula I: $R^1$, $R^4$, $R^5$ hydroxyl, $R^2$ and $R^3$ double bond | 15 | −40 | −31 | −13 | −12 | −20 | −22 | 4.74 | 1.26 |
| Lovastatin | 10 | −32 | −2 | −14 | −22 | −16 | −15 | 3.32 | 0.89 |
| Lovastatin | 50 | −52 | −26 | −15 | −40 | −19 | −38 | 4.29 | 1.14 |
| Lovastatin | 300 | −49 | +3 | −9 | −37 | +5 | −34 | 3.33 | 0.89 |
| Clofibrate | 100 | −46 | −31 | −26 | +5 | +2 | +2 | 4.03 | 1.08 |
| Control | | | | | | | | 3.75 | 1.00 |

TABLE 2

Rat, male, strain: HOE WISKf (SPF 71)

| No. of animals before/after | Compound | Dose in mg/kg/day | Serum enzymes | | | | | | | | Bilirubin (μmol/L) | | | | Creatinine (μmol/L) | | | |
|---|---|---|---|---|---|---|---|---|---|---|---|---|---|---|---|---|---|---|
| | | | SGOT | | SGPT (U/L) | | | | aP | (U/L) | | | | | | | | |
| | | | Initial | | Initial | | Final | | Initial | | Final | | Initial | | Final | | Initial | | Final |
| | | | x | s | x | s | x | s | x | s | x | s | x | s | x | s | x | s |
| 5/5 | Form. I; $R^1$ $R^4$, $R^5$ hydroxyl, $R^2$ and $R^3$ double bond | 15 | 41 | 2 | 56 | 12 | 29 | 3 | 25 | 5 | 359 | 21 | 247 | 43 | 2.8 0.4 | 2.0 0.4 | 67 | 5 | 64 | 7 |
| 5/5 | Lovastatin | 10 | 42 | 6 | 59 | 9 | 31 | 4 | 25 | 9 | 409 | 57 | 302 | 17 | 3.8 0.4 | 2.7 0.4 | 60 | 7 | 65 | 4 |
| 5/5 | Lovastatin | 50 | 38 | 3 | 89 | 57 | 31 | 7 | 46 | 16 | 355 | 23 | 324 | 148 | 2.9 0.2 | 2.5 0.2 | 60 | 6 | 62 | 7 |
| 5/5 | Lovastatin | 300 | 59 | 11 | 107 | 52 | 32 | 5 | 44 | 18 | 386 | 75 | 369 | 74 | 2.7 0.6 | 2.9 0.6 | 64 | 2 | 61 | 5 |

TABLE 2-continued

Rat, male, strain: HOE WISKf (SPF 71)

| No. of animals before/after | Compound | Dose in mg/kg/day | SGOT Initial (U/L) x, s | SGOT Final x, s | SGPT Initial (U/L) x, s | SGPT Final x, s | aP Initial (U/L) x, s | aP Final x, s | Bilirubin Initial (µmol/L) x, s | Bilirubin Final x, s | Creatinine Initial (µmol/L) x, s | Creatinine Final x, s |
|---|---|---|---|---|---|---|---|---|---|---|---|---|
| 20/19 | Control |  | 55  14 | 69  10 | 31  5 | 29  6 | 384  61 | 296  52 | 2.9  0.6 | 3.2  0.6 | 65  4 | 71  6 | x = mean
s = standard deviation

TABLE 3

Rat, male, strain: HOE WISKf (SPF 71)

% Change from control

| No. of animals before/after | Compound | Dose in mg/kg/day | Body weight after | Rel. liver weight after | rel. feed consumption after |
|---|---|---|---|---|---|
| 5/5 | Formula I; $R^1$, $R^4$, $R^5$ hydroxyl, $R^2$ and $R^3$ double bond | 15 | −3 |  | −1 |
| 5/5 | Lovastatin | 10 | +4 |  | +8 |
| 5/5 | Lovastatin | 50 | 0 |  | +4 |
| 5/5 | Lovastatin | 300 | +1 |  | +1 |
| 10/10 | Clofibrate | 100 | −2 | +19 | −2 |
| 20/19 | Control |  | 0 |  |  |

As is evident from Table 1, Formula I: $R^1$, $R^4$, $R^5$ hydroxyl, $R^2$ and $R^3$ double bond at only one seventh of the dose of clofibrate used results in an equally great reduction in the atherogenic serum lipoproteins LDL and VLDL (measured by means of their cholesterol content) and in a reduction which is only half as large in the HDL fraction. This results in a significant increase in the vasoprotective index HDL-cholesterol: LDL-cholesterol, which is likewise distinctly higher than with clofibrate. There is also a distinct reduction in the triglycerides, which are mainly transported in the VLDL, on use of the said compound. The competitive HMG-CoA reductase inhibitor lovastatin is distinctly inferior with regard to the effect on LDL-cholesterol, and about identical with regard to the effect on VLDL and HDL, to the compound according to the invention. The tolerability parameters, namely the serum enzymes SGOT, SGPT and aP, and serum bilirubin and serum creatinine are not pathologically changed by compound according to the invention, whereas lovastatin results in a dose-dependent and distinctly pathological change in the transaminase SGOT. The body weight gain and feed consumption are not changed in a relevant manner by the tested compounds, while the relative liver weight is increased by clofibrate, as generally known.

2. BIOLOGICAL TESTS AS CHOLESTEROL BIOSYNTHESIS INHIBITOR IN LIVER CELL CULTURES

Monolayers of HEP-G2 cells in liproprotein-free nutrient medium are preincubated with appropriate concentrations of the substances of the formula I to be tested for one hour. After addition of the $^{24}$C-labeled biosynthesis precursor sodium ($^{14}$C)acetate the incubation is continued for 3 hours. After this a portion of the cells is subjected to alkaline hydrolysis after addition of an internal standard of $^3$H-cholesterol. The lipids from the hydrolyzed cells are extracted with a chloroform/methanol mixture. This lipid mixture is, after addition of carrier cholesterol, fractionated by preparative thin-layer chromatography, the cholesterol band is stained and then isolated, and the amount of $^{14}$C-cholesterol formed from the $^{14}$C-precursor is determined by scintigraphy. Cellular protein was determined in an aliquot of the cells so that the amount of $^{14}$C-cholesterol formed from $^{14}$C-precursor per mg of cellular protein per unit time can be calculated. The control is used for comparison for the inhibitory effect of an added test product so that it is possible to state directly the inhibition of the cholesterol biosynthesis at a particular molar concentration of the test product in the medium. The integrity of the cell culture and the absence of cell damage owing to exposure to the product is assessed morphologically (light microscopy) and measured biochemically by determining the lactic dehydrogenase release into the incubation medium on aliquots of the cell culture.

The standard products used are lovastatin ($IC_{50}$: $2.3 \times 10^{-8}$ molar) and 25-hydroxycholesterol ($IC_{50}$ $2.3 \times 10^{-7}$ molar). The compound of the formula I in which $R^1$, $R^4$, $R^5$ are hydroxyl and $R^2$ and $R^3$ together form a double bond inhibits biosynthesis by 50% at $1 \times 10^{-7}$ molar; the cell culture is not damaged.

3. PREPARATION OF TABLETS

Tablets suitable for oral administration and containing the constituents specified below are prepared in a manner known per se by granulating the active substances and auxiliaries and subsequently compressing to tablets. These tablets are suitable for the treatment of diseases based on an elevated cholesterol level in a dose of one tablet 2–4 times a day.

| Constituents (per tablet) | Weight (mg) |
|---|---|
| Formula I: $R^1$, $R^4$, $R^5$ hydroxyl, $R^2$ and $R^3$ double bond | 50 mg |
| Lactose | 100 mg |
| Corn starch | 30 mg |
| Talc | 3 mg |
| Colloidal silica | 3 mg |
| Magnesium stearate | 2 mg |

4. PREPARATION OF CAPSULES

Capsules suitable for oral administration contain the constituents specified below and can be prepared in a manner known per se by mixing the active substances and auxiliaries and packing into gelatin capsules. These capsules are used to treat diseases based on an elevated cholesterol level in a dose of one capsule 2–4 times a day.

| Constituents (per capsule) | Weight (mg) |
|---|---|
| Formula I: $R^1$, $R^4$, $R^5$ hydroxyl, $R^2$ and $R^3$ double bond | 50 mg |
| Lactose | 100 mg |
| Corn starch | 30 mg |

| -continued | |
|---|---|
| Constituents (per capsule) | Weight (mg) |
| Talc | 3 mg |
| Colloidal silica | 3 mg |
| Magnesium stearate | 2 mg |

We claim:

1. A method for lowering serum cholesterol comprising administering to a mammal, in need of treatment for lowering serum cholesterol, a serum cholesterol lowering amount of a compound of the formula

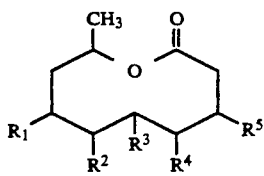

in which, independently of one another,
$R^1$ and $R^4$ are hydrogen or hydroxyl,
$R^2$ and $R^3$ are hydroxyl,
$R^5$ is hydrogen, hydroxyl or an oxo group, and
$R^2$ and $R^3$, and $R^3$ and $R^4$, can each together form a double bond.

2. A method for lowering serum cholesterol comprising administering to a mammal in need of treatment of lowering serum cholesterol, a serum cholesterol lowering amount of a compound of the formula I

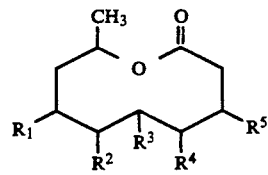

in which $R^1$, $R^4$ and $R^5$ are hydroxyl and $R^2$ and $R^3$ together form a double bond.

3. The method as claimed in claim 1 comprising orally administering a serum cholesterol lowering amount of a compound of the formula I.

* * * * *